(12) United States Patent
Takahashi et al.

(10) Patent No.: US 11,486,853 B2
(45) Date of Patent: Nov. 1, 2022

(54) GAS SENSOR AND PROTECTIVE COVER

(71) Applicant: NGK INSULATORS, LTD., Aichi (JP)

(72) Inventors: Fumiya Takahashi, Nagoya (JP); Takeshi Omori, Niwa-gun (JP)

(73) Assignee: NGK INSULATORS, LTD., Nagoya (JP)

( * ) Notice: Subject to any disclaimer, the term of this patent is extended or adjusted under 35 U.S.C. 154(b) by 116 days.

(21) Appl. No.: 17/038,109

(22) Filed: Sep. 30, 2020

(65) Prior Publication Data
US 2021/0102915 A1 Apr. 8, 2021

(30) Foreign Application Priority Data

Oct. 3, 2019 (JP) .............................. JP2019-183075

(51) Int. Cl.
| | |
|---|---|
| *G01N 27/407* | (2006.01) |
| *G01N 33/00* | (2006.01) |
| *G01D 11/24* | (2006.01) |
| *G01D 11/26* | (2006.01) |

(52) U.S. Cl.
CPC ....... *G01N 27/4078* (2013.01); *G01D 11/245* (2013.01); *G01D 11/26* (2013.01); *G01N 27/4077* (2013.01); *G01N 33/0036* (2013.01)

(58) Field of Classification Search
CPC ........... G01N 27/4077; G01N 27/4078; G01N 33/0036; G01D 11/245; G01D 11/26
USPC ................................ 204/409; 73/232, 31.05
See application file for complete search history.

(56) References Cited

U.S. PATENT DOCUMENTS

| | | | |
|---|---|---|---|
| 2004/0011646 A1* | 1/2004 | Nakagawa | ......... G01N 27/4077 204/426 |
| 2008/0156644 A1 | 7/2008 | Suzuki et al. | |
| 2015/0101394 A1 | 4/2015 | Fujita et al. | |
| 2016/0153814 A1* | 6/2016 | Seimori | ............. G01N 33/0054 73/431 |

(Continued)

FOREIGN PATENT DOCUMENTS

| | | |
|---|---|---|
| JP | 2008-164411 A | 7/2008 |
| JP | 2017-223620 A | 12/2017 |

OTHER PUBLICATIONS

Unexamined U.S. Appl. No. 17/038,099, filed Sep. 30, 2020.
(Continued)

*Primary Examiner* — John Fitzgerald
*Assistant Examiner* — Jean F Morello
(74) *Attorney, Agent, or Firm* — Mattingly & Malur, PC

(57) ABSTRACT

A gas sensor includes a sensor element, an inner protective cover including a first member and a second member, and an outer protective cover having outer inlets. The inner protective cover has a sensor element chamber inside. The outer protective cover and the inner protective cover form an inlet-side gas flow channel from an outside to the sensor element chamber. The inlet-side gas flow channel has a first flow channel extending in an upward direction from the outer inlets and a second flow channel extending in a downward direction. A ratio W2/W1 between a flow channel width W1 of the first flow channel and a flow channel width W2 of the second flow channel is less than one. A tip end portion of the outer protective cover has a tapered portion that reduces in diameter toward a bottom portion of the tip end portion.

9 Claims, 8 Drawing Sheets

(56) References Cited

U.S. PATENT DOCUMENTS

2017/0363596 A1  12/2017  Adachi et al.

OTHER PUBLICATIONS

Unexamined U.S. Appl. No. 17/038,103, filed Sep. 30, 2020.
Unexamined U.S. Appl. No. 17/038,110, filed Sep. 30, 2020.
Chinese Office Action received in corresponding Chinese Application No. 202011030603.8 dated Sep. 19, 2022.

* cited by examiner

GAS SENSOR AND PROTECTIVE COVER

The present application claims priority from Japanese Patent Application No. 2019-183075, filed on Oct. 3, 2019, the entire contents of which are incorporated herein by reference.

BACKGROUND OF THE INVENTION

1. Field of the Invention

The present invention relates to a gas sensor and a protective cover.

2. Description of the Related Art

Hitherto, a gas sensor that detects the concentration of predetermined gas, such as NOx and oxygen, in measurement-object gas, such as exhaust gas of automobiles, is known. For example, Patent Literature 1 describes a gas sensor including a sensor element, an inner protective cover in which the tip end of the sensor element is disposed, and an outer protective cover disposed outside the inner protective cover. Patent Literature 1 also describes that the response of gas concentration detection is enhanced by setting a cross-sectional area ratio S1/S2, which is the ratio between a total cross-sectional area S1 of one or more outer inlets that are disposed in the outer protective cover and that are inlets for measurement-object gas from an outside and a total cross-sectional area S2 of one or more outer outlets that are disposed in the outer protective cover and that are outlets for measurement-object gas to the outside, to a value greater than 2.0 and less than or equal to 5.0.

CITATION LIST

Patent Literature

PTL 1: JP 2017-223620 A

SUMMARY OF THE INVENTION

Incidentally, in such a gas sensor, it has been desired to further improve the response of gas concentration detection. Soot can be contained in measurement-object gas, and clogging of the protective cover due to soot may occur, with the result that the response can decrease. For this reason, it has also been desired to improve the soot resistance of a gas sensor.

The present invention is made to solve such inconvenience, and it is a main object to improve both the response and soot resistance of a gas sensor.

The present invention employs the following manner to achieve the above-described main object.

A gas sensor of the present invention includes:

a sensor element having a gas inlet port that introduces measurement-object gas and capable of detecting a specific gas concentration of the measurement-object gas having flowed in from the gas inlet port;

a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and a cylindrical outer protective cover including a cylindrical body portion having one or more outer inlets that are inlets for the measurement-object gas from an outside, and a bottomed cylindrical tip end portion having one or more outer outlets that are outlets for the measurement-object gas to the outside and smaller in inside diameter than the body portion, the outer protective cover being disposed outside the inner protective cover, wherein the outer protective cover and the inner protective cover form an inlet-side gas flow channel from the outside to the sensor element chamber, including the one or more outer inlets and the one or more element chamber inlets, and an outlet-side gas flow channel from the sensor element chamber to the outside, including the one or more element chamber outlets and the one or more outer outlets, the inner protective cover includes a cylindrical first member surrounding the sensor element, and a cylindrical second member surrounding the first member, where a direction parallel to an axial direction of the inner protective cover from the tip end of the sensor element toward a rear end of the sensor element is an upward direction and a direction from the rear end of the sensor element toward the tip end of the sensor element is a downward direction, the inlet-side gas flow channel has a first flow channel that is a space between the outer protective cover and the second member and that extends in the upward direction from the one or more outer inlets and a second flow channel that is a space between the second member and the first member, that is present between the first flow channel and the one or more element chamber inlets, and that extends in the downward direction, a ratio W2/W1 between a flow channel width W1 of the first flow channel and a flow channel width W2 of the second flow channel is less than one, the one or more outer inlets include at least two of three-type holes including a horizontal hole disposed at a side portion of the body portion of the outer protective cover, a vertical hole disposed at a bottom portion of the body portion, and a corner hole disposed at a corner portion at a boundary between the side portion and the bottom portion of the body portion, the tip end portion of the outer protective cover has a tapered portion that reduces in diameter toward a bottom portion of the tip end portion, and the one or more outer outlets include a vertical hole disposed at the bottom portion of the tip end portion of the outer protective cover.

In this gas sensor, measurement-object gas flowing around the gas sensor flows from the one or more outer inlets of the outer protective cover into the inlet-side gas flow channel and reaches the gas inlet port in the sensor element chamber from the inlet-side gas flow channel. Measurement-object gas in the sensor element chamber passes through the outlet-side gas flow channel and flows out from the one or more outer outlets to the outside. At this time, since the tip end portion of the outer protective cover has the tapered portion, stagnation of measurement-object gas is less likely to occur near the corner portion between the bottom portion and the side portion as compared to when the tip end portion has no tapered portion, that is, when the tip end portion has a bottom portion and a side portion connected perpendicularly to the bottom portion. Thus, measurement-object gas becomes easy to pass through the outlet-side gas flow channel and, as a result, measurement-object gas becomes easy to pass through the sensor element chamber, so the response of specific gas concentration detection of the gas sensor improves. In this gas sensor, the ratio W2/W1 between the flow channel width W1 of the first flow channel and the flow channel width W2 of the second flow channel in the inlet-side gas flow channel is less than one, so the flow channel width W1 is relatively large. Thus, even when soot having entered from the one or more outer inlets into the outer protective cover adheres to a wall surface of the first flow channel to some extent, clogging of the first flow channel due to soot is less likely to occur, so the soot resistance of the gas sensor improves. As described above, with this gas sensor, both the response and the soot resistance improve.

In the gas sensor of the present invention, the ratio W2/W1 may be greater than or equal to 0.43 and less than or equal to 0.82. When the ratio W2/W1 is less than or equal to 0.82, the flow channel width W1 tends to be relatively large, so clogging of the first flow channel is further reduced, and the soot resistance further improves. When the ratio W2/W1 is greater than or equal to 0.43, the flow channel width W2 is not too small, so measurement-object gas becomes easy to pass through the second flow channel, and the response of specific gas concentration detection improves. Even when the flow channel width W1 is large but the flow channel width W2 is too small, clogging of the second flow channel due to soot can occur; however, when the ratio W2/W1 is greater than or equal to 0.43, clogging of the second flow channel due to soot is reduced. As described above, when the ratio W2/W1 is greater than or equal to 0.43 and less than or equal to 0.82, both the response and the soot resistance further improve. In this case, the ratio W2/W1 may be greater than or equal to 0.45 and less than or equal to 0.65. With this configuration, both the response and the soot resistance further improve.

In the gas sensor of the present invention, the one or more outer inlets may include one or more of the at least horizontal hole of the three-type holes, and a minimum distance A in the axial direction between a center position of each of the one or more horizontal holes and an upper end of the second member may be greater than or equal to 7.3 mm. In other words, for any one of the one or more horizontal holes as well, the central position of each hole may be spaced apart by 7.3 mm or more in the downward direction from an upper end of the second member. When the minimum distance A is too small, it means that there is a horizontal hole that is too close to the upper end of the second member, that is, the upper end (downstream end) of the first flow channel. For this reason, the area of a surface in the first flow channel, in which soot having entered from such a horizontal hole into the outer protective cover deposits, is too small. Thus, clogging due to soot can become easy to occur in the first flow channel or soot is easy to reach the second flow channel and clogging due to soot can become easy to occur in the second flow channel. When the minimum distance A is greater than or equal to 7.3 mm, such clogging with soot is reduced, so the soot resistance improves.

In the gas sensor of the present invention, the flow channel width W1 may be greater than or equal to 1.20 mm and less than or equal to 1.70 mm, and the flow channel width W2 may be greater than or equal to 0.61 mm and less than or equal to 1.20 mm. In the gas sensor of the present invention, a sum Ws of the flow channel width W1 and the flow channel width W2 may be greater than or equal to 2.00 mm and less than or equal to 2.40 mm.

In the gas sensor of the present invention, the one or more element chamber inlets may be open in the downward direction. With this configuration, it is possible to reduce a situation in which measurement-object gas, flowing out from the one or more element chamber inlets, perpendicularly strikes the surface (surface other than the gas inlet port) of the sensor element and to reduce a situation in which measurement-object gas passes along the surface of the sensor element over a long distance and then reaches the gas inlet port. Thus, it is possible to suppress cooling of the sensor element. In addition, cooling of the sensor element is suppressed by adjusting the orientation of the opening of each element chamber inlet, and the flow rate or flow speed of measurement-object gas inside the inner protective cover is not reduced, so a decrease in the response of specific gas concentration detection is also reduced. With these configurations, it is possible to suppress a decrease in the heat retaining property of the sensor element while suppressing a decrease in the response of specific gas concentration detection. Here, the phrase "the one or more element chamber inlets are open in the downward direction" includes a case where each element chamber inlet is open parallel to the downward direction and a case where each element chamber inlet is open at an angle from the downward direction so as to approach the sensor element toward a lower side.

In the gas sensor of the present invention, the first member may have a first cylinder portion surrounding the sensor element, the second member may have a second cylinder portion larger in diameter than the first cylinder portion, and the second flow channel may be a cylindrical gap between an outer peripheral surface of the first cylinder portion and an inner peripheral surface of the second cylinder portion.

A protective cover of the present invention is a protective cover for protecting a sensor element having a gas inlet port that introduces measurement-object gas and capable of detecting a specific gas concentration of the measurement-object gas that has flowed in from the gas inlet port, and includes:

a cylindrical inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and a cylindrical outer protective cover including a cylindrical body portion having one or more outer inlets that are inlets for the measurement-object gas from an outside, and a bottomed cylindrical tip end portion having one or more outer outlets that are outlets for the measurement-object gas to the outside and smaller in inside diameter than the body portion, the outer protective cover being disposed outside the inner protective cover, wherein the outer protective cover and the inner protective cover form an inlet-side gas flow channel from the outside to the sensor element chamber, including the one or more outer inlets and the one or more element chamber inlets, and an outlet-side gas flow channel from the sensor element chamber to the outside, including the one or more element chamber outlets and the one or more outer outlets, the inner protective cover includes a cylindrical first member and a cylindrical second member surrounding the first member, where a direction parallel to an axial direction of the inner protective cover from the tip end portion of the outer protective cover toward the body portion is an upward direction and a direction from the body portion of the outer protective cover toward the tip end portion is a downward direction, the inlet-side gas flow channel has a first flow channel that is a space between the outer protective cover and the second member and that extends in the upward direction from the one or more outer inlets and a second flow channel that is a space between the second member and the first member, that is present between the first flow channel and the one or more element chamber inlets, and that extends in the downward direction, a ratio W2/W1 between a flow channel width W1 of the first flow channel and a flow channel width W2 of the second flow channel is less than one, the one or more outer inlets include at least two of three-type holes including a horizontal hole disposed at a side portion of the body portion of the outer protective cover, a vertical hole disposed at a bottom portion of the body portion, and a corner hole disposed at a corner portion at a boundary between the side portion and the bottom portion of the body portion, the tip end portion of the outer protective cover has a tapered portion that reduces in diameter toward a bottom portion of the tip end portion, and the one or more outer outlets include a vertical hole disposed at the bottom portion of the tip end portion of the outer protective cover.

By disposing the tip end of the sensor element and the gas inlet port in the sensor element chamber of the protective cover, an advantageous effect of improving both the response and soot resistance of the gas sensor is obtained as in the case of the above-described gas sensor of the present invention. In the protective cover of the present invention, various modes of the above-described gas sensor may be employed.

DETAILED DESCRIPTION OF THE INVENTION

Figure 1:
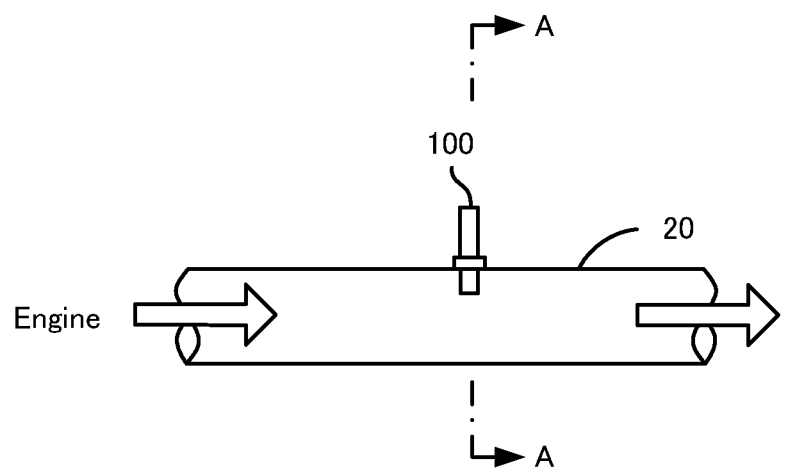
FIG. 1 is a schematic diagram of a state where a gas sensor 100 is attached to a pipe 20.
Figure 2:
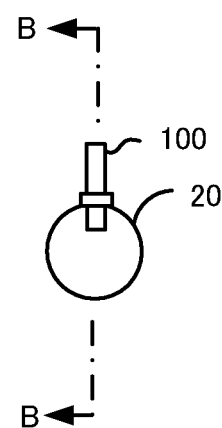
FIG. 2 is a cross-sectional view taken along the line A-A in FIG. 1.
Figure 3:
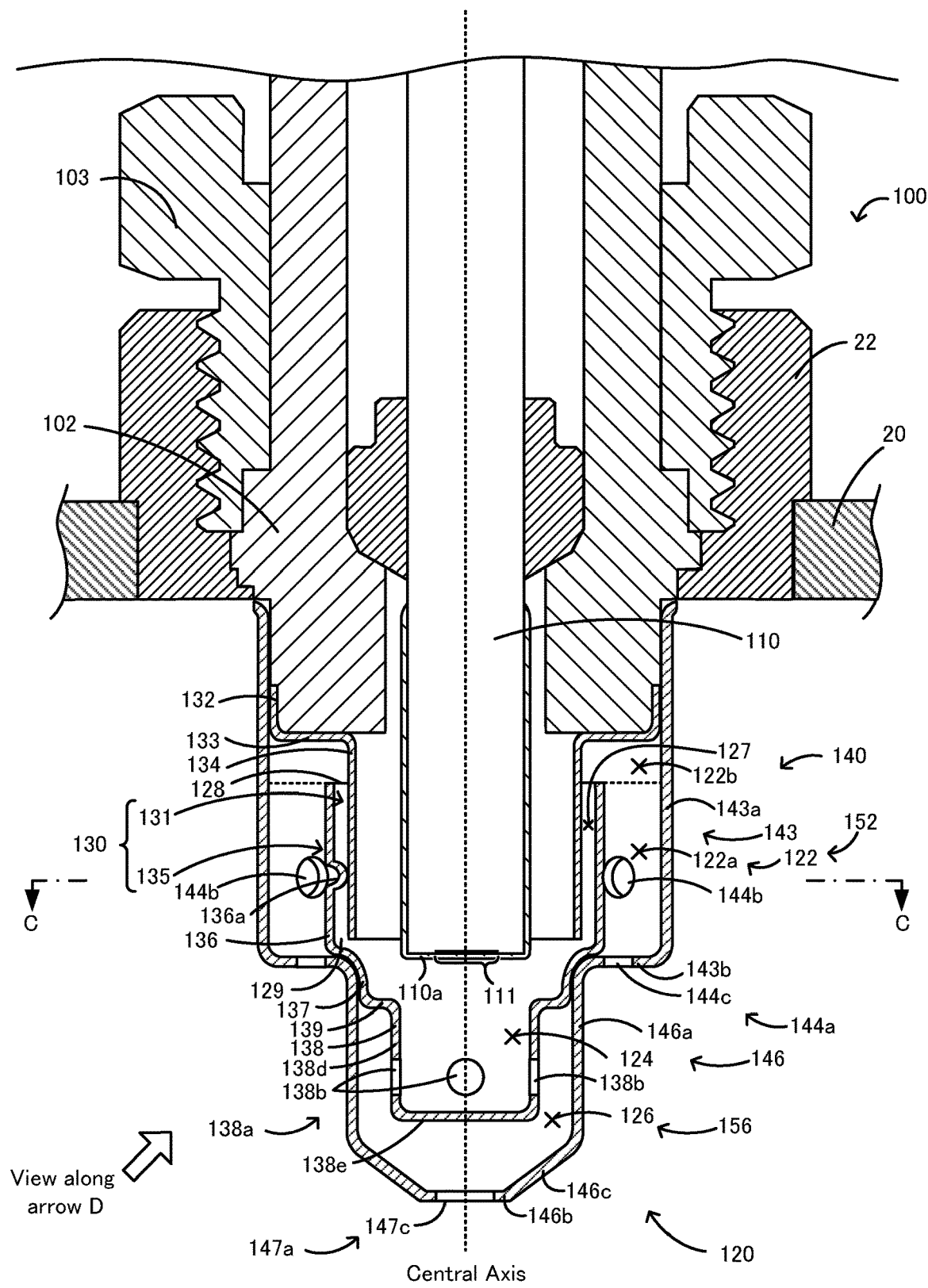
FIG. 3 is a cross-sectional view taken along the line B-B in FIG. 2.
Figure 4:
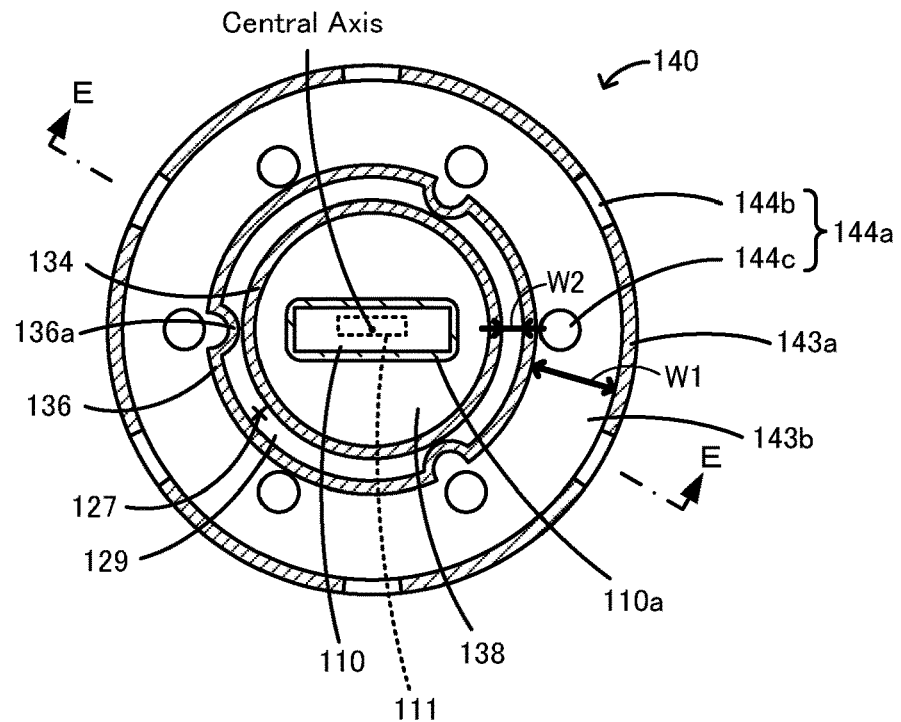
FIG. 4 is a cross-sectional view taken along the line C-C in FIG. 3.
Figure 5:
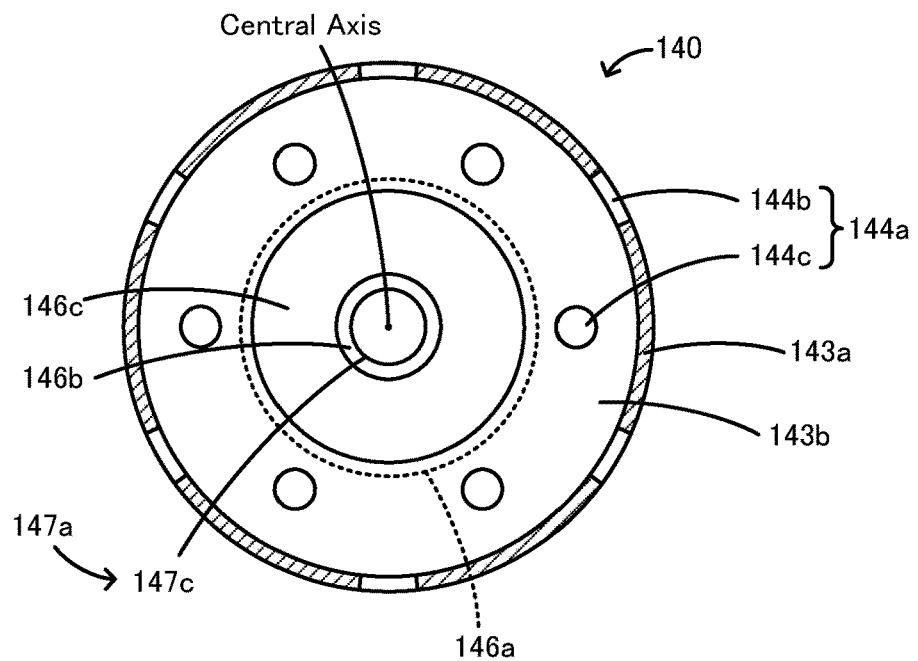
FIG. 5 is a cross-sectional view of an outer protective cover 140, taken along the line C-C in FIG. 3.
Figure 6:
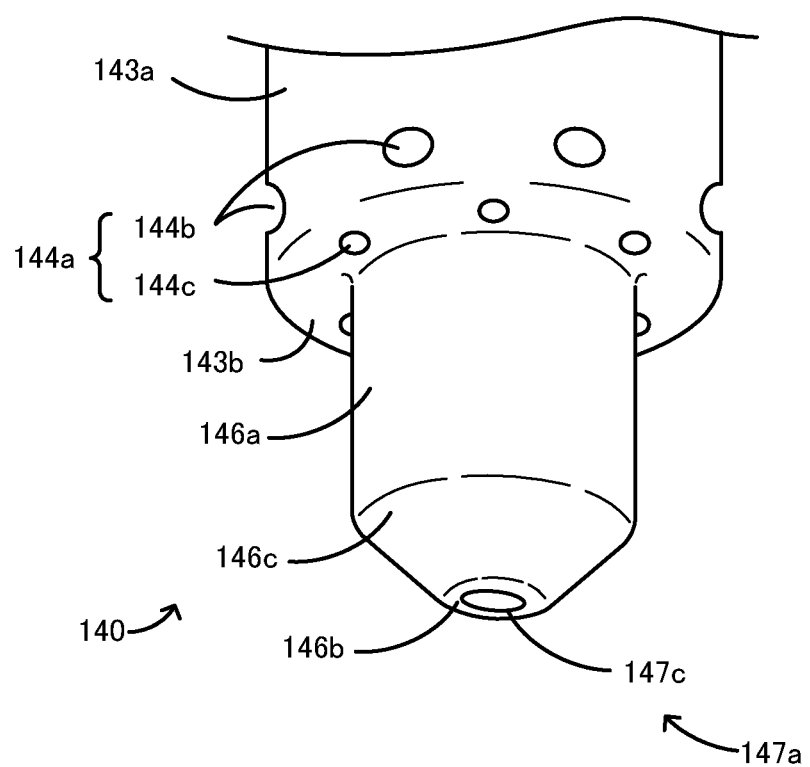
FIG. 6 is a view along the arrow D in FIG. 3.
Figure 7:
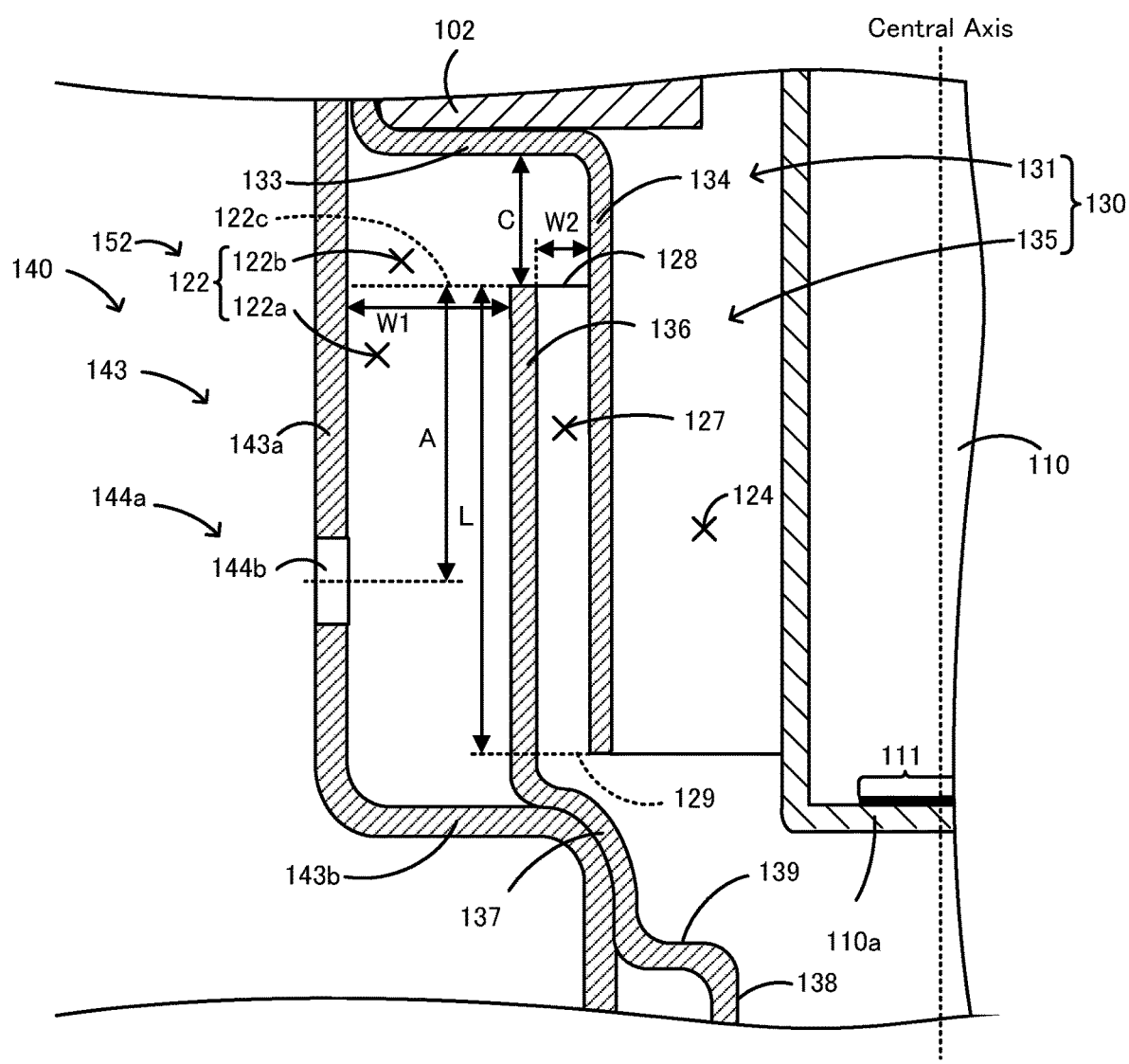
FIG. 7 is a partially enlarged cross-sectional view taken along the line E-E in FIG. 4.

Next, an embodiment of the present invention will be described with reference to the drawings. FIG. 1 is a schematic diagram of a state where a gas sensor 100 is attached to a pipe 20. FIG. 2 is a cross-sectional view taken along the line A-A in FIG. 1. FIG. 3 is a cross-sectional view taken along the line B-B in FIG. 2. FIG. 4 is a cross-sectional view taken along the line C-C in FIG. 3. FIG. 5 is a cross-sectional view of an outer protective cover 140, taken along the line C-C in FIG. 3. FIG. 5 corresponds to a diagram excluding a first cylinder portion 134, a second cylinder portion 136, a tip end portion 138, and a sensor element 110 from FIG. 4. FIG. 6 is a view along the arrow D in FIG. 3. FIG. 7 is a partially enlarged cross-sectional view taken along the line E-E in FIG. 4. A direction parallel to an axial direction of a protective cover 120 from a tip end of the sensor element 110 toward a rear end of the sensor element 110 (upward direction in FIG. 3 and FIG. 7) is defined as upward direction, and a direction parallel to the axial direction of the protective cover 120 from the rear end of the sensor element 110 toward the tip end of the sensor element 110 (downward direction in FIG. 3 and FIG. 7) is defined as downward direction.

As shown in FIG. 1, the gas sensor 100 is attached inside the pipe 20 that is an exhaust pathway from an engine of a vehicle and is configured to detect a specific gas concentration that is the concentration of at least any one specific gas of gas components, such as NOx, ammonia, and $O_2$, contained in exhaust gas as measurement-object gas emitted from the engine. As shown in FIG. 2, the gas sensor 100 is fixed to the pipe 20 in a state where a central axis of the gas sensor 100 is perpendicular to the flow of measurement-object gas in the pipe 20. The gas sensor 100 may be fixed to the pipe 20 in a state where the central axis of the gas sensor 100 is perpendicular to the flow of measurement-object gas in the pipe 20 and inclined at a predetermined angle (for example, 45°) with respect to a vertical direction.

As shown in FIG. 3, the gas sensor 100 includes the sensor element 110 having a function to detect a specific gas concentration (the concentration of NOx, ammonia, $O_2$, or the like) in measurement-object gas, and the protective cover 120 that protects the sensor element 110. The gas sensor 100 includes a metal housing 102 and a metal bolt 103 provided with external thread on its outer peripheral surface. The housing 102 is inserted in a fixing member 22 welded to the pipe 20 and provided with internal thread on its inner peripheral surface, and the housing 102 is fixed in the fixing member 22 by further inserting the bolt 103 into the fixing member 22. Thus, the gas sensor 100 is fixed to the pipe 20. A direction in which measurement-object gas flows inside the pipe 20 is a direction from the left toward the right in FIG. 3.

The sensor element 110 is an element having a narrow long planar shape and has such a structure that a plurality of oxygen-ion-conductive solid electrolyte layers made of zirconia ($ZrO_2$) or the like is laminated. The sensor element 110 has a gas inlet port 111 that introduces therein measurement-object gas and is configured to be capable of detecting a specific gas concentration of measurement-object gas having flowed in from the gas inlet port 111. In the present embodiment, the gas inlet port 111 is open at the tip end surface of the sensor element 110 (the lower surface of the sensor element 110 in FIG. 3). The sensor element 110 includes inside a heater that plays a role in temperature adjustment to retain temperature by heating the sensor element 110. The structure of the sensor element 110 and the principle of detecting a specific gas concentration are known and are described in, for example, Japanese Unexamined Patent Application Publication No. 2008-164411. The tip end (the lower end in FIG. 3) and gas inlet port 111 of the sensor element 110 are disposed inside the sensor element chamber 124. A direction from the rear end of the sensor element 110 toward the tip end of the sensor element 110 (downward direction) is also referred to as tip end direction.

The sensor element 110 includes a porous protective layer 110a that covers at least part of the surface. In the present embodiment, the porous protective layer 110a is formed on five surfaces out of six surfaces of the sensor element 110 and covers almost all the surface exposed to the inside of the sensor element chamber 124. Specifically, the porous protective layer 110a covers the entire tip end surface (lower surface) at which the gas inlet port 111 is formed in the sensor element 110. The porous protective layer 110a covers a side closer to the tip end surface of the sensor element 110 on the four surfaces (the upper, lower, right, and left surfaces of the sensor element 110 in FIG. 4) connected to the tip end surface of the sensor element 110. The porous protective layer 110a plays a role in, for example, suppressing occurrence of crack in the sensor element 110 as a result of adhesion of moisture or the like in measurement-object gas. The porous protective layer 110a also plays a role in suppressing adhesion of an oil component and the like contained in measurement-object gas to an electrode (not shown) or the like of the surface of the sensor element 110. The porous protective layer 110a is made of, for example, a porous material, such as alumina porous material, zirconia porous material, spinel porous material, cordierite porous material, titania porous material, and magnesia porous material. The porous protective layer 110a may be formed by, for example, plasma spraying, screen printing, dipping, or the like. The porous protective layer 110a also covers the gas inlet port 111; however, since the porous protective layer 110a is a porous material, so measurement-object gas is able to flow through the inside of the porous protective layer 110a and reach the gas inlet port 111. The thickness of the porous protective layer 110a is, for example, 100 μm to 700 μm.

The protective cover 120 is disposed so as to surround the sensor element 110. The protective cover 120 has a bottomed cylindrical inner protective cover 130 that covers the tip end of the sensor element 110 and a bottomed outer protective cover 140 that covers the inner protective cover 130. The sensor element chamber 124 is formed as a space surrounded by the inner protective cover 130. The outer protective cover 140 and the inner protective cover 130 form an inlet-side gas flow channel 152 that is a flow channel for measurement-object gas from the outside to the sensor element chamber 124, and an outlet-side gas flow channel 156 that is a flow channel for measurement-object gas from the sensor element chamber 124 to the outside. A first gas chamber 122 and a second gas chamber 126 are formed as spaces surrounded by the inner protective cover 130 and the outer protective cover 140. The first gas chamber 122 is part of the inlet-side gas flow channel 152. The second gas chamber 126 is part of the outlet-side gas flow channel 156. The central axes of the gas sensor 100, the sensor element 110, the inner protective cover 130, and the outer protective cover 140 are coaxial with one another. The protective cover 120 is made of metal (for example, stainless steel, such as SUS310S).

The inner protective cover 130 includes a first member 131 and a second member 135. The first member 131 has a cylindrical large-diameter portion 132, a cylindrical first cylinder portion 134 smaller in diameter than the large-diameter portion 132, and a stepped portion 133 that connects the large-diameter portion 132 and the first cylinder portion 134. The first cylinder portion 134 surrounds the sensor element 110. The second member 135 has a second cylinder portion 136 larger in diameter than the first cylinder portion 134, a tip end portion 138 located on a side in the tip end direction (downward direction) of the sensor element 110 with respect to the second cylinder portion 136, a stepped portion 139 disposed so as to be connected to the upper end of the tip end portion 138 and protruding outward from the outer peripheral surface of the tip end portion 138, and a connection portion 137 connecting the lower end of the second cylinder portion 136 and the stepped portion 139. The tip end portion 138 has a side portion 138d and a bottom portion 138e. The tip end portion 138 has one or more element chamber outlets 138a that communicate with the sensor element chamber 124 and the second gas chamber 126 and that are outlets for measurement-object gas from the sensor element chamber 124. The element chamber outlets 138a include a plurality of (four in the present embodiment) horizontal holes 138b formed at equal intervals at the side portion 138d. The element chamber outlets 138a are not disposed at the bottom portion 138e of the tip end portion 138. The diameter of each element chamber outlet 138a is, for example, 0.5 mm to 2.6 mm. In the present embodiment, the diameter of each of the plurality of horizontal holes 138b is set to the same value. The element chamber outlets 138a are formed at positions on a side in the tip end direction (downward direction) of the sensor element 110 with respect to the gas inlet port 111. In other words, the element chamber outlets 138a are located away (in the downward direction) from the gas inlet port 111 when viewed from the rear end of the sensor element 110 (the upper end (not shown) of the sensor element 110 in FIG. 3).

The large-diameter portion 132, the first cylinder portion 134, the second cylinder portion 136, and the tip end portion 138 have the same central axis. The inner peripheral surface of the large-diameter portion 132 is in contact with the housing 102. Thus, the first member 131 is fixed to the housing 102. In the second member 135, the outer peripheral surface of the connection portion 137 is in contact with the inner peripheral surface of the outer protective cover 140 and is fixed to the inner peripheral surface of the outer protective cover 140 by welding or the like. The second member 135 may be fixed by forming the outside diameter of the tip end side (lower end side) of the connection portion 137 so as to be slightly larger than the inside diameter of the tip end portion 146 of the outer protective cover 140 and press-fitting the tip end portion of the connection portion 137 into the tip end portion 146.

A plurality of protruding portions 136a that protrude toward the outer peripheral surface of the first cylinder portion 134 and that are in contact with the outer peripheral surface are formed on the inner peripheral surface of the second cylinder portion 136. As shown in FIG. 4, three protruding portions 136a are provided and are disposed equally on the inner peripheral surface of the second cylinder portion 136 along the circumferential direction. Each protruding portion 136a is formed in a substantially semispherical shape. With the thus configured protruding portions 136a, the positional relation between the first cylinder portion 134 and the second cylinder portion 136 is easily fixed by the protruding portions 136a. It is desirable that the protruding portions 136a press the outer peripheral surface of the first cylinder portion 134 radially inward. With this configuration, it is possible to further reliably fix the positional relation between the first cylinder portion 134 and the second cylinder portion 136 with the protruding portions 136a. The number of the protruding portions 136a is not limited to three and may be two or may be more than or equal to four. Because fixing of the first cylinder portion 134 to the second cylinder portion 136 tends to be stable, it is desirable that the number of the protruding portions 136a be more than or equal to three.

The inner protective cover 130 forms a second flow channel 127 (see FIG. 3, FIG. 4, and FIG. 7) that is a space between the first member 131 and the second member 135 and that is part of the inlet-side gas flow channel 152. More specifically, the second flow channel 127 is formed as a cylindrical gap (gas flow channel) between the outer peripheral surface of the first cylinder portion 134 and the inner peripheral surface of the second cylinder portion 136. The second flow channel 127 is a space from the upper end of the second member 135 (here, the upper end of the second cylinder portion 136) to the lower end of the first member 131 (here, the lower end of the first cylinder portion 134). The second flow channel 127 has a second flow channel inlet 128 that is an opening adjacent to the first gas chamber 122 that is a space in which the outer inlets 144a are disposed, and a second flow channel outlet 129 that is an opening adjacent to the sensor element chamber 124 that is a space in which the gas inlet port 111 is disposed. The second flow channel inlet 128 is a ring-shaped gap between the upper end of the inner peripheral surface of the second cylinder portion 136 and the outer peripheral surface of the first cylinder portion 134. The second flow channel outlet 129 is a ring-shaped gap between the inner peripheral surface of the second cylinder portion 136 and the lower end of the outer peripheral surface of the first cylinder portion 134. The second flow channel inlet 128 is formed adjacent to the rear end (upper side) of the sensor element 110 with respect to the second flow channel outlet 129. Therefore, during the pathway of measurement-object gas from the outer inlets 144a to the gas inlet port 111, that is, in the inlet-side gas flow channel 152, the second flow channel 127 is a flow channel from the rear end side (upper side) of the sensor element 110 toward the tip end side (lower side) of the sensor element 110. The second flow channel 127 is a flow channel parallel to a rear end-tip end direction (a flow channel parallel to the up-down direction) of the sensor element 110. The second flow channel outlet 129 is open to the sensor element chamber 124 and also serves as an element chamber inlet that is an inlet for measurement-object gas to the sensor element chamber 124. The second flow channel 127 is a flow channel for measurement-object gas, present between the first gas chamber 122 and the element chamber inlet.

The element chamber inlet (here, the second flow channel outlet 129) is open in a direction from the rear end of the sensor element 110 toward the tip end of the sensor element 110 (downward direction) and is open parallel to the rear end-tip end direction (up-down direction) of the sensor element 110. In other words, the second flow channel outlet 129 is open parallel to the downward direction. Therefore, the sensor element 110 is disposed at a position other than a region that is an imaginary extension of the second flow channel 127 from the second flow channel outlet 129 (a region just below the second flow channel outlet 129 in FIG. 3 and FIG. 7). Thus, it is possible to reduce a situation in which measurement-object gas flowing out from the second flow channel outlet 129 directly strikes the surface of the sensor element 110, so it is possible to suppress cooling of the sensor element 110.

As shown in FIG. 3, the outer protective cover 140 has a cylindrical body portion 143 and a bottomed cylindrical tip end portion 146 smaller in inside diameter than the body portion 143. The body portion 143 has a side portion 143a having a side surface along a central axis direction (up-down direction) of the outer protective cover 140, and a stepped portion 143b that is a bottom portion of the body portion 143 and that connects the side portion 143a and the tip end portion 146. The central axes of the body portion 143 and the tip end portion 146 all are the same as the central axis of the inner protective cover 130. A part around the upper end in the body portion 143 is in contact with the housing 102 and the large-diameter portion 132 on its inner peripheral surface. Thus, the outer protective cover 140 is fixed to the housing 102. The body portion 143 is located so as to cover the outer circumference of the large-diameter portion 132, the first cylinder portion 134, and the second cylinder portion 136. The tip end portion 146 is located so as to cover the tip end portion 138, and the inner peripheral surface is in contact with the outer peripheral surface of the connection portion 137. The tip end portion 146 has a side portion 146a having a side surface along the central axis direction (up-down direction) of the outer protective cover 140 and of which the outside diameter is smaller than the inside diameter of the side portion 143a, a bottom portion 146b that is the bottom portion of the outer protective cover 140, and a tapered portion 146c that connects the side portion 146a and the bottom portion 146b and that reduces in diameter from the side portion 146a toward the bottom portion 146b. The tip end portion 146 is located on a side in the tip end direction (on the lower side) with respect to the body portion 143. The outer protective cover 140 has one or more (in the present embodiment, multiple and, specifically, 12) outer inlets 144a that are formed in the body portion 143 and that are inlets for measurement-object gas from the outside, and one or more outer outlets 147a that are formed in the tip end portion 146 and that are outlets for measurement-object gas to the outside.

The outer inlets 144a are holes that communicate with the outer side (outside) of the outer protective cover 140 and the first gas chamber 122. The outer inlets 144a include a plurality of (in the present embodiment, six) horizontal holes 144b formed at equal intervals in the side portion 143a, and a plurality of (in the present embodiment, six) vertical holes 144c formed at equal intervals in the stepped portion 143b (see FIG. 3 to FIG. 6). The outer inlets 144a (horizontal holes 144b and vertical holes 144c) are holes perforated in a circular shape. The diameter of each of the 12 outer inlets 144a is, for example, 0.5 mm to 2 mm. The diameter of each outer inlet 144a may be less than or equal to 1.5 mm. In the present embodiment, the diameter of each of the plurality of horizontal holes 144b is the same value, and the diameter of each of the plurality of vertical holes 144c is the same value. The diameter of each horizontal hole 144b is greater than the diameter of each vertical hole 144c. As shown in FIG. 4 and FIG. 5, the outer inlets 144a are formed such that the horizontal hole 144b and the vertical hole 144c are alternately located at equal intervals along the circumferential direction of the outer protective cover 140. In other words, an angle formed between a line connecting the center of the horizontal hole 144b and the central axis of the outer protective cover 140 and a line connecting the center of the vertical hole 144c adjacent to that horizontal hole 144b and the central axis of the outer protective cover 140 in FIG. 4 and FIG. 5 is 30° (360°/12).

The outer outlets 147a are holes that communicate with the outer side (outside) of the outer protective cover 140 and the second gas chamber 126. The outer outlets 147a include one or more (in the present embodiment, one) vertical holes 147c formed at the center of the bottom portion 146b of the tip end portion 146 (see FIG. 3, FIG. 5, and FIG. 6). Different from the outer inlets 144a, the outer outlet 147a is not disposed at the side portion of the outer protective cover 140 (here, the side portion 146a of the tip end portion 146). The outer outlet 147a (here, the vertical hole 147c) is a hole perforated in a circular shape. The diameter of the outer outlet 147a is, for example, 0.5 mm to 2.5 mm. The diameter of the outer outlet 147a may be less than or equal to 1.5 mm. In the present embodiment, the diameter of the vertical hole 147c is set to a value greater than the diameter of the horizontal hole 144b or the vertical hole 144c.

The outer protective cover 140 and the inner protective cover 130 form the inlet-side gas flow channel 152 and the outlet-side gas flow channel 156 as described above. The inlet-side gas flow channel 152 includes the outer inlets 144a, the first gas chamber 122, the second flow channel 127, and the element chamber inlet (here, the second flow channel outlet 129), and measurement-object gas passes through the inlet-side gas flow channel 152 in this order. The outlet-side gas flow channel 156 includes the element chamber outlets 138a, the second gas chamber 126, and the outer outlet 147a, and measurement-object gas passes through the outlet-side gas flow channel 156 in this order. The first gas chamber 122 is formed as a space between the body portion 143 and the inner protective cover 130. More specifically, the first gas chamber 122 is a space surrounded by the stepped portion 133, the first cylinder portion 134, the second cylinder portion 136, the side portion 143a, and the stepped portion 143b. The second gas chamber 126 is formed as a space between the tip end portion 146 and the inner protective cover 130. More specifically, the second gas chamber 126 is a space surrounded by the tip end portion 138 and the tip end portion 146. Since the inner peripheral surface of the tip end portion 146 is in contact with the outer peripheral surface of the connection portion 137, the first gas chamber 122 and the second gas chamber 126 do not directly communicate with each other.

As shown in FIG. 7, the first gas chamber 122 has a first flow channel 122a and a space 122b. The first flow channel 122a is a space between the outer protective cover 140 and the second member 135 of the inner protective cover 130 and functions as a flow channel for measurement-object gas that flows in the upward direction from the outer inlets 144a. The first flow channel 122a is, more specifically, a space surrounded by the side portion 143a, the stepped portion 143b, and the second cylinder portion 136 and is a space below the upper end of the second member 135 (here, the upper end of the second cylinder portion 136). The first flow channel 122a is a cylindrical gap between the inner peripheral surface of the outer protective cover 140 and the outer peripheral surface of the second cylinder portion 136. The space 122b is a space above the upper end of the second member 135 (here, the upper end of the second cylinder portion 136) between the outer protective cover 140 and the first member 131 (here, the first cylinder portion 134). The space 122b functions as a flow channel for measurement-object gas from the first flow channel 122a to the second flow channel 127. The space 122b is a cylindrical gap between the inner peripheral surface of the outer protective cover 140 and the outer peripheral surface of the first cylinder portion 134.

An inflow port for measurement-object gas from the first flow channel 122a to the space 122b is referred to as first flow channel outlet 122c. The first flow channel outlet 122c is a ring-shaped gap between the inner peripheral surface of the outer protective cover 140 and the upper end of the outer peripheral surface of the second cylinder portion 136. All the outer inlets 144a are located below the first flow channel outlet 122c. In other words, all the outer inlets 144a are located below the upper end of the second member 135 (here, the upper end of the second cylinder portion 136).

Here, the flow channel width of the first flow channel 122a is denoted by W1, and the flow channel width of the second flow channel 127 is denoted by W2. The flow channel width W1 is the radial width of the first flow channel 122a and is the difference between a radius Ar1 of the inner peripheral surface of the side portion 143a of the body portion 143 and a radius Ar2 of the outside diameter of the second cylinder portion 136. The flow channel width W2 is the radial width of the second flow channel 127 and is the difference between a radius Br1 of the inside diameter of the second cylinder portion 136 and a radius Br2 of the outside diameter of the first cylinder portion 134. The first flow channel 122a is a flow channel parallel to the up-down direction. The flow channel width W1 is the same value at any location in the first flow channel 122a. Similarly, the second flow channel 127 is a flow channel parallel to the up-down direction. The flow channel width W2 is the same value at any location in the second flow channel 127. A ratio W2/W1 between the flow channel width W1 and the flow channel width W2 is less than one. In other words, W1>W2. It is desirable that the ratio W2/W1 be greater than or equal to 0.43 and less than or equal to 0.82, and it is more desirable that the ratio W2/W1 be greater than or equal to 0.45 and less than or equal to 0.65. The flow channel width W1, the flow channel width W2, and the ratio W2/W1 are able to be adjusted by adjusting the radii Ar1, Ar2, Br1, Br2. These radii satisfy Ar1>Ar2>Br1>Br2. The flow channel width W1 may be, for example, greater than or equal to 1.18 mm, or may be greater than or equal to 1.20 mm, or may be greater than or equal to 1.3 mm. The flow channel width W1 may be less than or equal to 1.85 mm, or may be less than or equal to 1.70 mm, or may be less than or equal to 1.60 mm, or may be less than or equal to 1.5 mm. The flow channel width W2 may be, for example, greater than or equal to 0.51 mm, or may be greater than or equal to 0.61 mm. The flow channel width W2 may be less than or equal to 1.20 mm, or may be less than or equal to 1.18 mm, or may be less than or equal to 1.06 mm, or may be less than or equal to 0.85 mm. A sum Ws of the flow channel width W1 and the flow channel width W2 may be, for example, greater than or equal to 2.00 mm and less than or equal to 2.40 mm. The radius Ar1 may be, for example, greater than or equal to 6.9 mm and less than or equal to 7.2 mm. The radius Br2 may be, for example, greater than or equal to 4.2 mm and less than or equal to 4.8 mm.

A flow channel length L of the second flow channel 127 is, for example, greater than 0 mm and less than or equal to 8.3 mm. In the present embodiment, the flow channel length L is equal to the distance in the up-down direction between second flow channel inlet 128 and the second flow channel outlet 129. The flow channel length L may be greater than or equal to 3.0 mm or may be greater than or equal to 4.0 mm. The flow channel length L may be less than or equal to 7.0 mm, or may be less than or equal to 6.6 mm, or may be less than or equal to 5 mm.

The length of the space 122b in the up-down direction is referred to as height C. The height C may be, for example, greater than or equal to 0.47 mm or may be greater than or equal to 0.75 mm. The height C may be less than or equal to 3.80 mm, or may be less than or equal to 2.35 mm, or may be less than or equal to 1.87 mm.

Next, the flow of measurement-object gas inside the protective cover 120 at the time when the gas sensor 100 detects a specific gas concentration will be described. Measurement-object gas that flows in the pipe 20 initially passes through at least any one of the plurality of outer inlets 144a (here, the horizontal holes 144b and the vertical holes 144c) and flows into the first gas chamber 122. Subsequently, measurement-object gas passes through the first flow channel 122a, the space 122b, and the second flow channel 127 in this order, flows out from the second flow channel outlet 129, and flows into the sensor element chamber 124. Measurement-object gas having flowed from the second flow channel outlet 129 into the sensor element chamber 124 at least partially reaches the gas inlet port 111 of the sensor element 110. When measurement-object gas reaches the gas inlet port 111 and flows into the inside of the sensor element 110, the sensor element 110 generates an electrical signal (voltage or current) according to a specific gas concentration in the measurement-object gas, and the specific gas concentration is detected based on the electrical signal. Measurement-object gas in the sensor element chamber 124 flows into the second gas chamber 126 through at least any one of the element chamber outlets 138a (here, the horizontal holes 138b) and flows out from there to the outside through the outer outlet 147a. The output of a heater inside the sensor element 110 is controlled by a controller (not shown) such that the sensor element 110 is maintained at a predetermined temperature.

Here, in the gas sensor 100 of the present embodiment, the tip end portion 146 of the outer protective cover 140 has the tapered portion 146c. Therefore, in comparison with the case where the tip end portion 146 has no tapered portion 146c, that is, in comparison with the case where the bottom portion 146b of the tip end portion 146 and the side portion 146a perpendicular to the bottom portion 146b are directly connected, there is no corner portion bent at right angles between the bottom portion 146b and the side portion 146a. With such a corner portion bent at right angles, stagnation of measurement-object gas tends to occur near the corner portion, so measurement-object gas becomes difficult to pass through the outlet-side gas flow channel 156. In the gas sensor 100 of the present embodiment, there is no such a corner portion bent at right angles, so measurement-object gas becomes easy to pass through the outlet-side gas flow channel 156, with the result that measurement-object gas becomes easy to pass through the sensor element chamber 124. With this configuration, the response of specific gas concentration detection of the gas sensor 100 improves. Soot can be contained in measurement-object gas that flows in the pipe 20. When clogging due to soot occurs in the flow channel for measurement-object gas in the protective cover 120, the response of specific gas concentration detection can decrease. In the gas sensor 100 of the present embodiment, the ratio W2/W1 between the flow channel width W1 of the first flow channel 122a and the flow channel width W2 of the second flow channel 127 in the inlet-side gas flow channel 152 is less than one (that is, W1>W2), so the flow channel width W1 is relatively large. Thus, even when soot having entered from the outer inlets 144a into the outer protective cover 140 adheres to the wall surface of the first flow channel 122a to some extent, clogging of the first flow channel 122a due to soot is less likely to occur, so the soot resistance of the gas sensor 100 improves. As described above, with the gas sensor 100 of the present embodiment, both the response and the soot resistance improve. The ratio W2/W1 may be greater than or equal to 0.3.

It is desirable that the ratio W2/W1 be greater than or equal to 0.43 and less than or equal to 0.82. When the ratio W2/W1 is less than or equal to 0.82, the flow channel width W1 tends to be relatively large, so clogging of the first flow channel 122a is further reduced, and the soot resistance further improves. When the ratio W2/W1 is greater than or equal to 0.43, the flow channel width W2 is not too small, so measurement-object gas becomes easy to pass through the second flow channel 127, and the response of specific gas concentration detection improves. Even when the flow channel width W1 is large but the flow channel width W2 is too small, clogging of the second flow channel 127 due to soot can occur; however, when the ratio W2/W1 is greater than or equal to 0.43, clogging of the second flow channel 127 due to soot is suppressed. As described above, when the ratio W2/W1 is greater than or equal to 0.43 and less than or equal to 0.82, both the response and the soot resistance further improve. It is desirable that the ratio W2/W1 be greater than or equal to 0.45 and less than or equal to 0.65, it is more desirable that the ratio W2/W1 be greater than or equal to 0.48 and less than or equal to 0.59, and it is further more desirable that the ratio W2/W1 be greater than or equal to 0.52 and less than or equal to 0.56.

It is desirable that a minimum distance A (see FIG. 7) in the up-down direction between the center position of each of the horizontal holes 144b of the outer inlets 144a and the upper end of the second member 135 be greater than or equal to 7.3 mm. In other words, it is desirable that, for any of the one or more horizontal holes 144b, the center position of the hole be spaced apart by 7.3 mm or longer in the downward direction from the upper end of the second member 135. When the minimum distance A is too small, it means that there is a horizontal hole 144b that is too close to the upper end of the second member 135, that is, the upper end (downstream end) of the first flow channel 122a. For this reason, the area of a surface in the first flow channel 122a in which soot having entered from such a horizontal hole 144b into the outer protective cover 140 deposits is too small. Thus, clogging due to soot can easily occur in the first flow channel 122a or soot easily reaches the second flow channel 127 and clogging due to soot can easily occur in the second flow channel 127. When the minimum distance A is greater than or equal to 7.3 mm, such clogging with soot is reduced, so the soot resistance improves. The minimum distance A may be less than or equal to 8.1 mm.

With the gas sensor 100 of the present embodiment described in detail above, since the tip end portion 146 of the outer protective cover 140 has the tapered portion 146c, the response of specific gas concentration detection improves. When the ratio W2/W1 is less than one, the soot resistance of the gas sensor 100 improves. Therefore, with the gas sensor 100, both the response and the soot resistance improve.

When the ratio W2/W1 is greater than or equal to 0.43 and less than or equal to 0.82, both the response and the soot resistance further improve. When the ratio W2/W1 is greater than or equal to 0.45 and less than or equal to 0.65, both the response and the soot resistance further improve. When the minimum distance A is greater than or equal to 7.3 mm, the soot resistance improves.

Since the element chamber inlet (here, the second flow channel outlet 129) is open in the downward direction, it is possible to reduce a situation in which measurement-object gas, flowing out from the element chamber inlet, perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to suppress cooling of the sensor element 110. In addition, cooling of the sensor element 110 is suppressed by adjusting the orientation of the opening of the element chamber inlet, and the flow rate or flow speed of measurement-object gas inside the inner protective cover 130 is not reduced, so a decrease in the response of specific gas concentration detection is also reduced. With these configurations, it is possible to suppress a decrease in the heat retaining property of the sensor element 110 while suppressing a decrease in the response of specific gas concentration detection.

The present invention is not limited to the above-described embodiment and may be, of course, implemented in various modes within the technical scope of the present invention.

Figure 8:
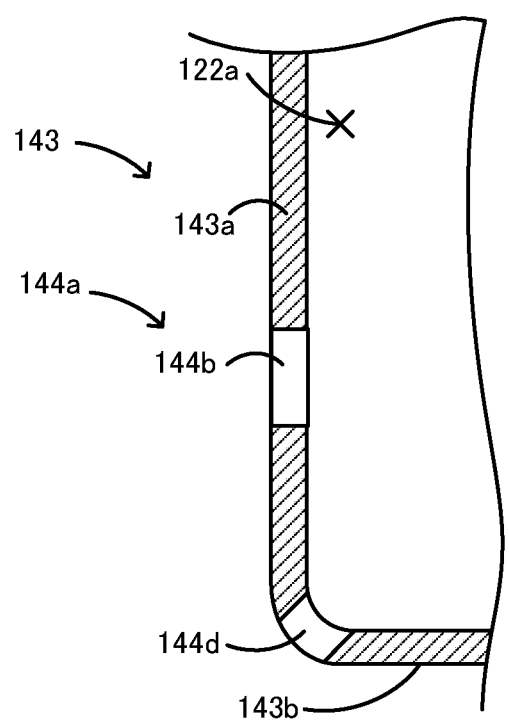
FIG. 8 is a partial cross-sectional view when outer inlets 144a include corner holes 144d.

For example, in the above-described embodiment, the outer inlets 144a include the horizontal holes 144b and the vertical holes 144c; however, the configuration is not limited thereto. It is sufficient that the outer inlets 144a include at least two-type holes out of three-type holes of the horizontal hole 144b disposed at the side portion 143a of the body portion 143 of the outer protective cover 140, the vertical hole 144c disposed at the bottom portion (stepped portion 143b) of the body portion 143, and the corner hole disposed at the corner portion at the boundary between the side portion 143a and bottom portion (stepped portion 143b) of the body portion 143. For example, as shown in FIG. 8, the outer inlets 144a may include the horizontal holes 144b and corner holes 144d. FIG. 8 shows the case where the horizontal holes 144b and the corner holes 144d are disposed at positions of the same phases with reference to the central axis of the outer protective cover 140. Alternatively, as in the case of the horizontal holes 144b and the vertical holes 144c in FIG. 3, a plurality of the horizontal holes 144b and a plurality of the corner holes 144d may be disposed alternately at equal intervals. Instead, the horizontal holes 144b and the vertical holes 144c in FIG. 3 may be disposed at positions of the same phases as shown in FIG. 8. When the outer inlets 144a include two-type or more holes out of three-type holes, that is, the horizontal hole 144b, the vertical hole 144c, and the corner hole 144d, measurement-object gas becomes easy to flow from the outer inlets 144a into the outer protective cover 140. It is desirable that the outer inlets 144a include at least one or more horizontal holes out of three-type holes. It is sufficient that the element chamber outlets 138a and the outer outlet 147a each include at least one or more types out of a horizontal hole, a vertical hole, and a corner hole. The outer outlets 147a may include a through-hole provided at the tapered portion 146c.

In the above-described embodiment, the diameter of each of the plurality of horizontal holes 144b is greater than the diameter of each of the plurality of vertical holes 144c; however, the magnitude relation in diameter is not limited thereto. The plurality of horizontal holes 144b and the plurality of vertical holes 144c each may have the same diameter, or the vertical holes 144c may be larger in diameter. All the diameters of the plurality of horizontal holes 144b do not need to be the same values or all the diameters of the plurality of vertical holes 144c do not need to be the same values.

In the above-described embodiment, the second flow channel outlet 129 of the second flow channel 127 also serves as the element chamber inlet; however, the configuration is not limited thereto. For example, the inlet-side gas flow channel 152 may further include another flow channel between the second flow channel outlet 129 of the second flow channel 127 and the element chamber inlet. In this case, the element chamber inlet, different from the second flow channel outlet 129, does not need to be open in the downward direction and may be open to the sensor element chamber 124 in a direction perpendicular to the downward direction. Regardless of whether the second flow channel outlet 129 also serves as the element chamber inlet, it is desirable that the element chamber inlet be open in the downward direction. In the above-described embodiment, the number of the element chamber inlets is one; however, it is sufficient that the number of the element chamber inlets be one or more.

In the above-described embodiment, the tip end portion 138 of the inner protective cover 130 has such a shape that the outside diameter of the side portion 138d is constant and the side portion 138d and the bottom portion 138e have the same diameters. Alternatively, the tip end portion 138 may have such a shape that the outside diameter of the side portion 138d reduces as it approaches the bottom portion 138e, for example, an inverted truncated cone shape or the like. In other words, the tip end portion 138 of the inner protective cover 130 may have a tapered portion. For example, instead of the tip end portion 138, a tip end portion 338 of FIG. 10 (described later) may be employed.

In the above-described embodiment, the protruding portions 136a are formed on the inner peripheral surface of the second cylinder portion 136; however, the configuration is not limited thereto. It is sufficient that a plurality of protruding portions is formed on at least one of the outer peripheral surface of the first cylinder portion 134 and the inner peripheral surface of the second cylinder portion 136 so as to protrude toward the other surface and contact with the other surface. In the above-described embodiment, as shown in FIG. 3 and FIG. 4, the outer peripheral surfaces of parts where the protruding portions 136a are formed in the second cylinder portion 136 are recessed inward; however, the configuration is not limited thereto. Alternatively, the outer peripheries do not need to be recessed. The protruding portions 136a are not limited to a semi-spherical shape and may have any shape. The protruding portions 136a do not need to be formed on the outer peripheral surface of the first cylinder portion 134 or on the inner peripheral surface of the second cylinder portion 136. Although not described in the above embodiment, even when the protruding portions 136a are present, measurement-object gas is able to flow through a region where there is no protruding portion 136a in the second flow channel 127, so it is assumed that the protruding portions 136a do not influence the value of the flow channel width W2. For example, as shown in FIG. 4, when viewed along the flow direction of measurement-object gas in the second flow channel 127, the value of the flow channel width W2 is determined based on the region where there is no protruding portion 136a. When viewed along the flow direction of measurement-object gas in the second flow channel 127, the percentage of reduction in the flow channel cross-sectional area of the second flow channel 127 due to the presence of the protruding portions 136a may be lower than or equal to 20% or may be lower than or equal to 15% or may be lower than or equal to 10%. For example, in the above-described embodiment, the percentage of reduction is calculated as {(the absolute value of a reduction in the cross-sectional area of the second flow channel 127 due to the protruding portions 136a in the cross section of FIG. 4)×(the number of protruding portions 136a)}/{(the area of a circle having the inside diameter of the second cylinder portion 136 as a diameter)−(the area of a circle having the outside diameter of the first cylinder portion 134 as a diameter)}×100%.

Figure 9:
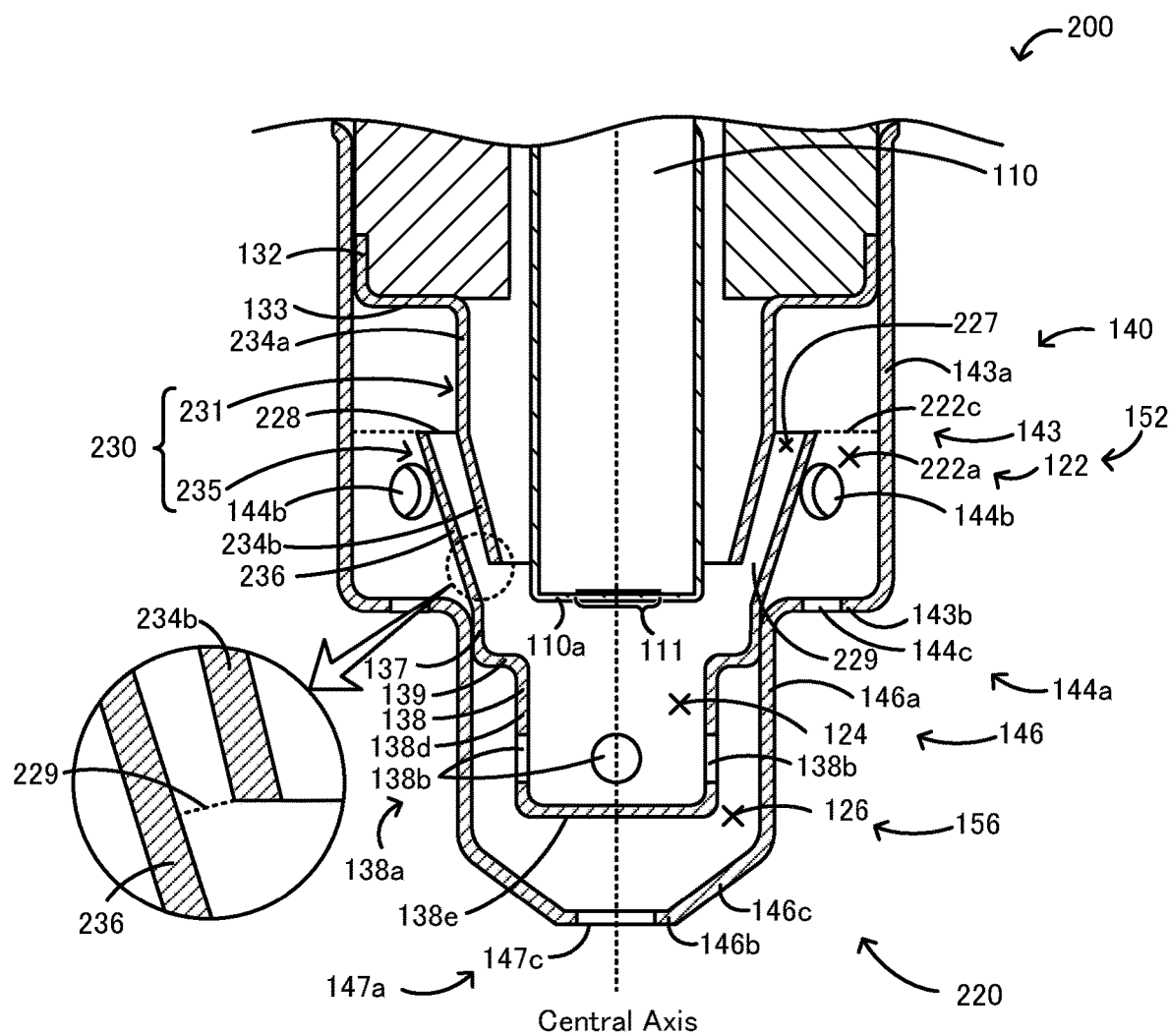
FIG. 9 is a longitudinal sectional view of a gas sensor 200 of a modification.

In the above-described embodiment, the second flow channel 127 is a cylindrical gap between the first cylinder portion 134 of the first member 131 and the second cylinder portion 136 of the second member 135; however, the configuration is not limited thereto. It is sufficient that the second flow channel 127 is a space between the first member 131 and the second member 135 and is a flow channel extending in the downward direction. For example, the second flow channel 127 is a flow channel parallel to the rear end-tip end direction of the sensor element 110 (a flow channel parallel to the up-down direction in FIG. 3). Alternatively, the second flow channel 127 may be a flow channel inclined at an angle with respect to the up-down direction so as to approach the sensor element 110 toward the lower side. FIG. 9 is a longitudinal sectional view of a gas sensor 200 of a modification in this case. In FIG. 9, like reference signs are assigned to the same components as those of the gas sensor 100, and the detailed description thereof is omitted. As shown in FIG. 9, a protective cover 220 of the gas sensor 200 includes an inner protective cover 230 instead of the inner protective cover 130. The inner protective cover 230 includes a first member 231 and a second member 235. The first member 231, as compared to the first member 131, includes a cylindrical body portion 234a and a cylindrical first cylinder portion 234b that reduces in diameter toward the lower side, instead of the first cylinder portion 134. The first cylinder portion 234b is connected to the body portion 234a at its upper end portion. The second member 235, as compared to the second member 135, includes a cylindrical second cylinder portion 236 that reduces in diameter toward the lower side, instead of the second cylinder portion 136. The outer peripheral surface of the first cylinder portion 234b and the inner peripheral surface of the second cylinder portion 236 are not in contact with each other, and a gap formed therebetween is a second flow channel 227. The second flow channel 227 includes a second flow channel inlet 228 that is an opening adjacent to the first gas chamber 122 and a second flow channel outlet 229 (which also serves as an element chamber inlet) that is an opening adjacent to the sensor element chamber 124. The second flow channel 227 is a flow channel inclined at an angle with respect to the up-down direction so as to approach the sensor element 110 (so as to approach the central axis of the inner protective cover 230) toward the lower side according to the shapes of the first cylinder portion 234b and the second cylinder portion 236. Similarly, the element chamber inlet (second flow channel outlet 229) is open at an angle with respect to the up-down direction so as to approach the sensor element 110 toward the downward side (see the enlarged view in FIG. 9). It is assumed that the direction of the opening of the element chamber inlet (second flow channel outlet 229) is the axial direction of the opening determined based on the outer peripheral surface of the first cylinder portion 234b and the inner peripheral surface of the second cylinder portion 236 near the opening. An opening plane of the element chamber inlet (second flow channel outlet 229) is a plane perpendicular to the axial direction of the opening. The flow channel width of the second flow channel 227 narrows toward the lower side of the sensor element 110. The space between the first cylinder portion 234b and the body portion 143 is a first flow channel 222a. With this gas sensor 200 as well, similar advantageous effects are obtained with similar characteristics of the above-described gas sensor 100. For example, when the ratio W2/W1 between the flow channel width W1 of the first flow channel 222a and the flow channel width W2 of the second flow channel 227 is less than one, clogging of the first flow channel 222a due to soot is less likely to occur, so the soot resistance of the gas sensor 200 improves. Here, the second cylinder portion 236 is inclined with respect to the up-down direction, and the flow channel width of the first flow channel 222a is not constant. In such a case, a minimum value of the flow channel width of the first flow channel 222a is set as the flow channel width W1. In the gas sensor 200, the flow channel width is narrowest at the point of the first flow channel outlet 222c of the first flow channel 222a, so the flow channel width of this point is set as the flow channel width W1. Similarly, the flow channel width is narrowest at the point of the second flow channel outlet 229 of the second flow channel 227, so the flow channel width of this point is set as the flow channel width W2.

When the second flow channel 227 is a flow channel inclined with respect to the up-down direction or when the element chamber inlet (second flow channel outlet 229) is open at an angle with respect to the up-down direction as in the case of the gas sensor 200 of FIG. 9, the direction of flow of measurement-object gas that flows from the element chamber inlet to the sensor element chamber 124 is a direction inclined at an angle with respect to the up-down direction. Thus, similar advantageous effects to those of the second flow channel 127 or the second flow channel outlet 129 of the above-described embodiment are obtained. In other words, it is possible to reduce a situation in which measurement-object gas perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to suppress cooling of the sensor element 110. In FIG. 9, the flow channel width of the second flow channel 227 narrows toward the lower side of the sensor element 110. Therefore, the opening area of the second flow channel outlet 229 is less than the opening area of the second flow channel inlet 228. Thus, when measurement-object gas flows in from the second flow channel inlet 228 and flows out from the second flow channel outlet 229, the flow speed of measurement-object gas increases at the time of flowing out as compared to at the time of flowing in. Therefore, it is possible to improve the response of specific gas concentration detection. In FIG. 9, the second flow channel 227 is a flow channel inclined at an angle with respect to the up-down direction, the element chamber inlet (second flow channel outlet 229) is open at an angle with respect to the up-down direction, and the opening area of the second flow channel outlet 229 is less than the opening area of the second flow channel inlet 228. Alternatively, one or more of these three features may be omitted, or a gas sensor may have one or more of these three features.

In the above-described embodiment, the inner protective cover 130 includes two members, that is, the first member 131 and the second member 135. Alternatively, the first member 131 and the second member 135 may be an integrated member.

In the above-described embodiment, the gas inlet port 111 is open at the tip end surface of the sensor element 110 (the lower surface of the sensor element 110 in FIG. 3); however, the configuration is not limited thereto. For example, the gas inlet port 111 may be open at the side surface of the sensor element 110 (the surface, extending in the up-down direction, of the sensor element 110 in FIG. 4).

In the above-described embodiment, the sensor element 110 includes the porous protective layer 110a. Alternatively, the sensor element 110 does not need to include the porous protective layer 110a.

In the above-described embodiment, the protective cover 120 is described as part of the gas sensor 100. Alternatively, the protective cover 120 may be distributed solely.

EXAMPLES

Hereinafter, specific examples of a manufactured gas sensor will be described as examples. The present invention is not limited to the following examples.

Example 1

The gas sensor 100 shown in FIG. 3 to FIG. 7 was assumed as Example 1. In Example 1, the radius Ar1 of the inner peripheral surface of the side portion 143a of the body portion 143, the radius Ar2 of the outside diameter of the second cylinder portion 136, the radius Br1 of the inside diameter of the second cylinder portion 136, and the radius Br2 of the outside diameter of the first cylinder portion 134 were adjusted such that the flow channel width W1 was 1.3 mm, the flow channel width W2 was 0.85 mm, and the ratio W2/W1 was 0.65. Specifically, the radius Ar1 was set to 7.20 mm, the radius Ar2 was set to 5.90 mm, the radius Br1 was set to 5.60 mm, and the radius Br2 was set to 4.75 mm. Of the outer inlets 144a, the diameter of each of six horizontal holes 144b was set to 1.5 mm, and the diameter of each of six vertical holes 144c was set to 1 mm. The six horizontal holes 144b were disposed at positions where the minimum distance A was 7.3 mm.

Examples 2 to 5

Examples 2 to 5 were configured similarly to the gas sensor 100 of Example 1 except that the flow channel widths W1, W2, and the ratio W2/W1 were changed to the values shown in Table 1. In Examples 1 to 5, the value of the sum Ws each was set to the same, that is, 2.15 mm, and only the balance between the flow channel width W1 and the flow channel width W2 was changed. In Examples 2 to 5, the radii Ar1, Br2 were set to the same as those of Example 1, and the flow channel widths W1, W2 were changed by changing the radii Ar2, Br1 from those of Example 1.

Comparative Example 1

Figure 10:
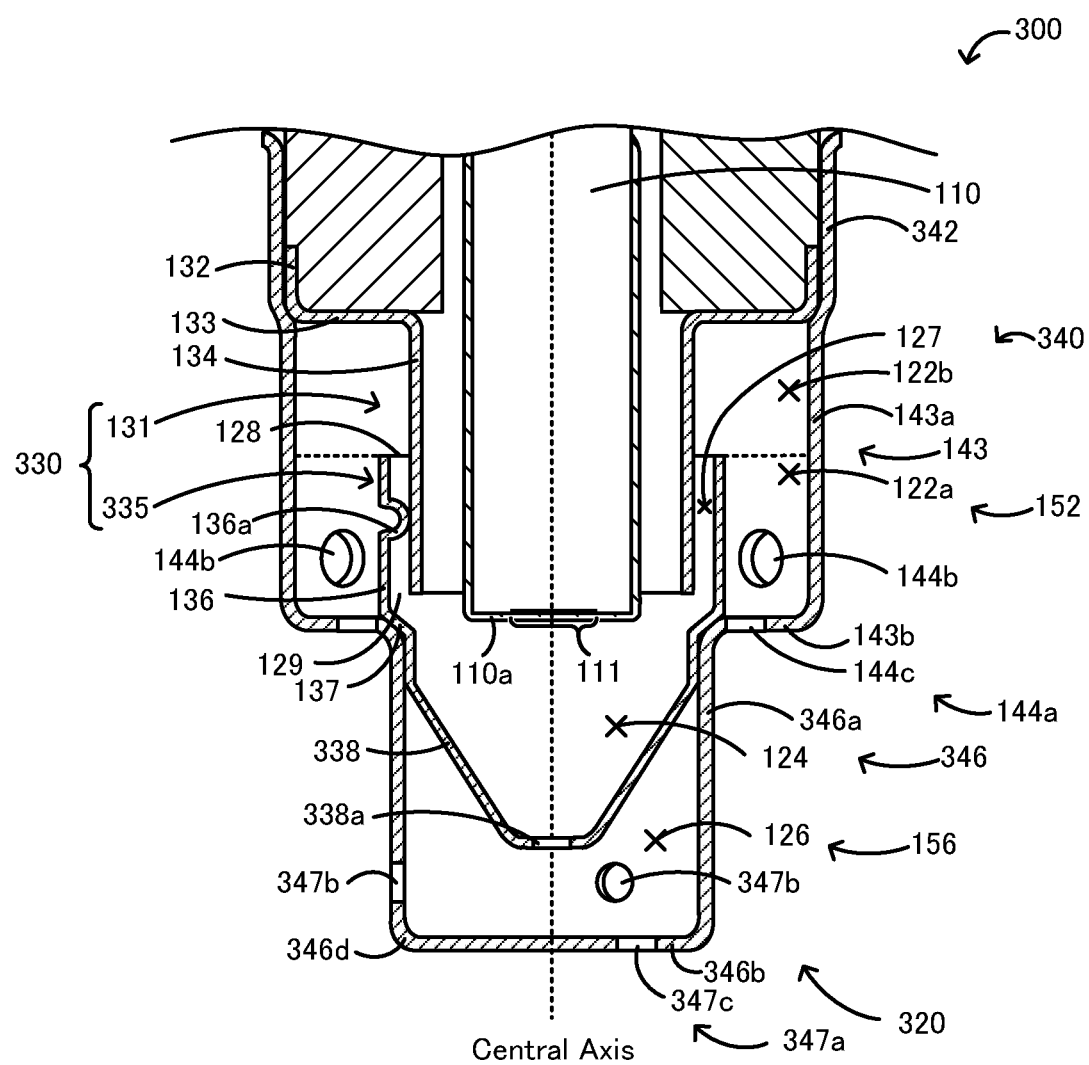
FIG. 10 is a longitudinal sectional view of a gas sensor 300 of Comparative Example 1.

A gas sensor 300 shown in FIG. 10 was set as Comparative Example 1. In FIG. 10, like reference signs are assigned to the same components as those of the gas sensor 100, and the detailed description thereof is omitted. As shown in FIG. 10, a protective cover 320 of the gas sensor 300 includes an inner protective cover 330 instead of the inner protective cover 130, and includes an outer protective cover 340 instead of the outer protective cover 140. A second member 335 of the inner protective cover 330 has a tip end portion 338 having an inverted truncated cone shape, instead of the tip end portion 138 and the stepped portion 139 in FIG. 3. The tip end portion 338 has an element chamber outlet 338a that communicates with the sensor element chamber 124 and the second gas chamber 126 and that is an outlet for measurement-object gas from the sensor element chamber 124. The element chamber outlet 338a is a single circular vertical hole formed at the center of the bottom surface of the tip end portion 338. The outer protective cover 340 has a cylindrical large-diameter portion 342 larger in diameter than the body portion 143 above the body portion 143. In the outer protective cover 340, not the body portion 143 but the inner peripheral surface of the large-diameter portion 342 is in contact with the housing 102 and the large-diameter portion 132. The outer protective cover 340 has a bottomed cylindrical (cylindrical) tip end portion 346 smaller in inside diameter than the body portion 143, instead of the tip end portion 146 of FIG. 3. The tip end portion 346 has a side portion 346a having a side surface along the central axis direction (up-down direction in FIG. 10) of the outer protective cover 340 and of which the outside diameter is smaller than the inside diameter of the side portion 143a, and a bottom portion 346b that is the bottom portion of the outer protective cover 340. The tip end portion 346 does not include the tapered portion 146c as in the case of the tip end portion 146 of FIG. 3, and the bottom portion 346b and the side portion 346a perpendicular to the bottom portion 146b are directly connected. Therefore, the tip end portion 346 includes a corner portion 346d bent at right angles. Outer outlets 347a that are outlets for measurement-object gas to the outside are formed at the tip end portion 346. The outer outlets 347a include three horizontal holes 347b formed at equal intervals along the circumferential direction of the outer protective cover 340 at the side portion 346a of the tip end portion 346, and three vertical holes 347c formed at equal intervals along the circumferential direction of the outer protective cover 340 at the bottom portion 346b. The horizontal holes 347b and the vertical holes 347c are located alternately at equal intervals along the circumferential direction of the outer protective cover 340, and an angle (phase) formed between the adjacent horizontal hole 347b and vertical hole 347c is 60°. In Comparative Example 1, the flow channel width W1 was set to 1.73 mm, the flow channel width W2 was set to 0.60 mm, and the ratio W2/W1 was set to 0.35. Of the outer inlets 144a, the diameter of each of six horizontal holes 144b was set to 1.5 mm, and the diameter of each of six vertical holes 144c was set to 1 mm. By reducing the length of the second cylinder portion 136 in the up-down direction as compared to Example 1, the minimum distance A was set to 3.6 mm.

Comparative Example 2

Comparative Example 2 was configured similarly to the gas sensor 300 of Comparative Example 1 except that the minimum distance A was set to 2.0 mm by moving the positions of the horizontal holes 144b upward and the outer outlets 347a did not include the horizontal holes 347b but included the six vertical holes 347c disposed at equal intervals.

Comparative Example 3

In Comparative Example 3, by setting the same radii Ar1, Ar2, Br1, Br2 as those of Example 5, the flow channel widths W1, W2 and the ratio W2/W1 were the same values as those of Example 5 (W1 was 1.5 mm, W2 was 0.65 mm, and the ratio W2/W1 was 0.43). In Comparative Example 3, by setting the same length of the second cylinder portion 136 in the up-down direction as that of Example 5, the minimum distance A was set to the same value (7.3 mm) as that of Example 5. Other than the above, Comparative Example 3 was configured similarly to the gas sensor 300 of Comparative Example 1.

Examples 6 to 9

Examples 6 to 9 were configured similarly to the gas sensor 100 of Example 1 except that the flow channel widths W1, W2 and the ratio W2/W1 were changed to the values shown in Table 1 and the minimum distance A was set to 8.1 mm greater than 7.3 mm by reducing the height C. In Examples 6 to 9, the value of the sum Ws was set to the same, that is, 2.36 mm, by reducing the radius Br2 as compared to Examples 1 to 5. In Examples 6 to 9, the value of the sum Ws was set to the same, and the balance between the flow channel width W1 and the flow channel width W2 was varied from one another.

Comparative Example 4

Comparative Example 4 was configured similarly to the gas sensors 100 of Examples 6 to 9 except that the flow channel widths W1, W2 and the ratio W2/W1 were changed to the values shown in Table 1. In Comparative Example 4, the values of the radius Ar1, the radius Br2, and the sum Ws were set to the same values as those of Examples 6 to 9, and the ratio W2/W1 was made greater than one by setting the balance between the flow channel width W1 and the flow channel width W2 to a value different from that of Examples 6 to 9.

[Evaluation of Response]

The gas sensors of Examples 1 to 9 and Comparative Examples 1 to 4 each were connected to a pipe similarly as shown in FIG. 1 and FIG. 2. Gas obtained by adjusting the atmosphere by mixture of oxygen into a selected oxygen concentration at a temperature of 350° C. was used as measurement-object gas, and the measurement-object gas was caused to flow in the pipe at a flow speed of 1 m/s. Then, a temporal change in the output of the sensor element in the case where the oxygen concentration of measurement-object gas to be caused to flow in the pipe was changed from 23.6% to 20.9% was investigated. Where the output value of the sensor element just before the oxygen concentration was changed was 0% and the output value at the time when the output of the sensor element after a change of the oxygen concentration varied and then became stable was 100%, an elapsed time from when the output value exceeds 10% to when the output value exceeds 90% was defined as a response time [s] of specific gas concentration detection. It means that the response of specific gas concentration detection increases as the response time shortens. Measurement of a response time was performed multiple times for each test example, and the average of each was determined as a response time for an associated test example. The response was evaluated where "A (Excellent)" was assigned for the case where the response time was shorter than or equal to 4.6 seconds, "B (Good)" was assigned for the case where the response time was longer than 4.6 seconds and shorter than or equal to 4.8 seconds, "C (Pass)" was assigned for the case where the response time was longer than 4.8 seconds and shorter than or equal to 5.0 seconds, and "F (Fail)" was assigned for the case where the response time was longer than 5.0 seconds. The results are shown in Table 1.

[Evaluation of Soot Resistance]

For the gas sensors of Examples 1 to 9 and Comparative Examples 1 to 4, the response time after a sooting process was measured, and the soot resistance was evaluated. The sooting process was performed as follows. Initially, the gas sensors were connected to a pipe similarly as shown in FIG. 1 and FIG. 2. Subsequently, gas with a soot amount of 15 g/h and a gas flow rate of 3 $Nm^3$/min was caused to flow in the pipe by producing burning with a gas burner on the upstream side of the pipe, and the gas sensors were exposed to the gas for 48 hours. After that, except that measurement-object gas was caused to flow at a flow speed of 7 m/s, the same test as the above-described method of measuring the response time was performed, and the response time after the sooting process was measured. It means that the soot resistance increases as the response time after the sooting process shortens. The soot resistance was evaluated where "A (Excellent)" was assigned for the case where the response time was shorter than or equal to 5.0 seconds, "B (Good)" was assigned for the case where the response time was longer than 5.0 seconds and shorter than or equal to 5.5 seconds, "C (Pass)" was assigned for the case where the response time was longer than 5.5 seconds and shorter than or equal to 6.0 seconds, and "F (Fail)" was assigned for the case where the response time was longer than 6.0 seconds. The results are shown in Table 1.

TABLE 1

|  | Flow Channel Width W1 [mm] | Flow Channel Width W2 [mm] | Ratio W2/W1 | Sum Ws [mm] | Minimum Distance A [mm] | Whether a tip end portion of an outer protective cover has a tapered portion or not | Response | Soot Resistance |
| --- | --- | --- | --- | --- | --- | --- | --- | --- |
| Example 1 | 1.30 | 0.85 | 0.65 | 2.15 | 7.3 | Yes | A | C |
| Example 2 | 1.35 | 0.80 | 0.59 | 2.15 | 7.3 | Yes | A | B |
| Example 3 | 1.40 | 0.75 | 0.54 | 2.15 | 7.3 | Yes | A | A |
| Example 4 | 1.45 | 0.70 | 0.48 | 2.15 | 7.3 | Yes | B | B |
| Example 5 | 1.50 | 0.65 | 0.43 | 2.15 | 7.3 | Yes | C | C |
| Comparative Example 1 | 1.73 | 0.60 | 0.35 | 2.33 | 3.6 | No | F | F |
| Comparative Example 2 | 1.73 | 0.60 | 0.35 | 2.33 | 2.0 | No | F | F |
| Comparative Example 3 | 1.50 | 0.65 | 0.43 | 2.15 | 7.3 | No | F | C |
| Example 6 | 1.75 | 0.61 | 0.35 | 2.36 | 8.1 | Yes | C | C |
| Example 7 | 1.60 | 0.76 | 0.48 | 2.36 | 8.1 | Yes | B | B |
| Example 8 | 1.45 | 0.91 | 0.63 | 2.36 | 8.1 | Yes | A | C |
| Example 9 | 1.30 | 1.06 | 0.82 | 2.36 | 8.1 | Yes | C | C |
| Comparative Example 4 | 1.15 | 1.21 | 1.05 | 2.36 | 8.1 | Yes | F | F |

As is apparent from Table 1, when Example 5 and Comparative Example 3 in which the flow channel widths W1, W2, the ratio W2/W1, and the minimum distance A all were the same were compared with each other, Example 5 having the tapered portion 146c had a higher response than Comparative Example 3 having no tapered portion 146c. This is presumably because, in Comparative Example 3, since the corner portion 346d bent at right angles is present between the bottom portion 346b and the side portion 346a, stagnation of measurement-object gas occurs near the corner portion 346d in the second gas chamber 126 and, as a result, measurement-object gas becomes difficult to pass through the outlet-side gas flow channel 156. In Examples 1 to 9 that satisfy the condition that the tapered portion 146c is provided and the ratio W2/W1 is less than one, the response and the soot resistance of each were evaluated as higher than or equal to "C (Pass)", and both the response and the soot resistance were high. In contrast, in Comparative Examples 1 to 3 having no tapered portion 146c and Comparative Example 4 having the ratio W2/W1 greater than or equal to one, the response of each was "F (Fail)", and, for Comparative Examples 1, 2, and 4, the soot resistance was also "F (Fail)". From the results of Examples 1 to 9, presumably, it is desirable that the ratio W2/W1 be greater than or equal to 0.43 and less than or equal to 0.82, and it is more desirable that the ratio W2/W1 be greater than or equal to 0.45 and less than or equal to 0.65. From comparison among Examples 1 to 9, it is presumable that both the response and the soot resistance are evaluated as higher than or equal to "B (Good)" when the ratio W2/W1 is greater than or equal to 0.48 and less than or equal to 0.59 and both the response and the soot resistance are "A (Excellent)" when the ratio W2/W1 is greater than or equal to 0.52 and less than or equal to 0.56. It was found from comparison among Examples 1 to 9 that, even when the minimum distance A was any one of 7.3 mm and 8.1 mm, both the response and the soot resistance were high when the condition in which the tapered portion 146c was provided and the ratio W2/W1 was less than one was satisfied.

What is claimed is:

1. A gas sensor comprising:
a sensor element having a gas inlet port that introduces measurement-object gas and capable of detecting a specific gas concentration of the measurement-object gas having flowed in from the gas inlet port;
a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and
a cylindrical outer protective cover including a cylindrical body portion having one or more outer inlets that are inlets for the measurement-object gas from an outside, and a bottomed cylindrical tip end portion having one or more outer outlets that are outlets for the measurement-object gas to the outside and smaller in inside diameter than the body portion, the outer protective cover being disposed outside the inner protective cover, wherein
the outer protective cover and the inner protective cover form an inlet-side gas flow channel from the outside to the sensor element chamber, including the one or more outer inlets and the one or more element chamber inlets, and an outlet-side gas flow channel from the sensor element chamber to the outside, including the one or more element chamber outlets and the one or more outer outlets,
the inner protective cover includes a cylindrical first member surrounding the sensor element, and a cylindrical second member surrounding the first member,
where a direction parallel to an axial direction of the inner protective cover from the tip end of the sensor element toward a rear end of the sensor element is an upward direction and a direction from the rear end of the sensor element toward the tip end of the sensor element is a downward direction, the inlet-side gas flow channel has a first flow channel that is a space between the outer protective cover and the second member and that extends in the upward direction from the one or more outer inlets and a second flow channel that is a space between the second member and the first member, that is present between the first flow channel and the one or more element chamber inlets, and that extends in the downward direction,
a ratio W2/W1 between a flow channel width W1 of the first flow channel and a flow channel width W2 of the second flow channel is less than one,
the one or more outer inlets include at least two of three-type holes including a horizontal hole disposed at a side portion of the body portion of the outer protective cover, a vertical hole disposed at a bottom portion of the body portion, and a corner hole disposed at a corner portion at a boundary between the side portion and the bottom portion of the body portion,
the tip end portion of the outer protective cover has a tapered portion that reduces in diameter toward a bottom portion of the tip end portion, and
the one or more outer outlets include a vertical hole disposed at the bottom portion of the tip end portion of the outer protective cover.

2. The gas sensor according to claim 1, wherein the ratio W2/W1 is greater than or equal to 0.43 and less than or equal to 0.82.

3. The gas sensor according to claim 1, wherein the ratio W2/W1 is greater than or equal to 0.45 and less than or equal to 0.65.

4. The gas sensor according to claim 1, wherein the one or more outer inlets include one or more of the at least horizontal hole of the three-type holes, and a minimum distance A in the axial direction between a center position of each of the one or more horizontal holes and an upper end of the second member is greater than or equal to 7.3 mm.

5. The gas sensor according to claim 1, wherein the flow channel width W1 is greater than or equal to 1.20 mm and less than or equal to 1.70 mm, and the flow channel width W2 is greater than or equal to 0.61 mm and less than or equal to 1.20 mm.

6. The gas sensor according to claim 1, wherein a sum Ws of the flow channel width W1 and the flow channel width W2 is greater than or equal to 2.00 mm and less than or equal to 2.40 mm.

7. The gas sensor according to claim 1, wherein the one or more element chamber inlets are open in the downward direction.

8. The gas sensor according to claim 1, wherein the first member has a first cylinder portion surrounding the sensor element,
the second member has a second cylinder portion larger in diameter than the first cylinder portion, and
the second flow channel is a cylindrical gap between an outer peripheral surface of the first cylinder portion and an inner peripheral surface of the second cylinder portion.

9. A protective cover for protecting a sensor element having a gas inlet port that introduces measurement-object gas and capable of detecting a specific gas concentration of the measurement-object gas that has flowed in from the gas inlet port, the protective cover comprising:
a cylindrical inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and
a cylindrical outer protective cover including a cylindrical body portion having one or more outer inlets that are inlets for the measurement-object gas from an outside, and a bottomed cylindrical tip end portion having one or more outer outlets that are outlets for the measurement-object gas to the outside and smaller in inside diameter than the body portion, the outer protective cover being disposed outside the inner protective cover, wherein
the outer protective cover and the inner protective cover form an inlet-side gas flow channel from the outside to the sensor element chamber, including the one or more outer inlets and the one or more element chamber inlets, and an outlet-side gas flow channel from the sensor element chamber to the outside, including the one or more element chamber outlets and the one or more outer outlets, the inner protective cover includes a cylindrical first member and a cylindrical second member surrounding the first member, where a direction parallel to an axial direction of the inner protective cover from the tip end portion of the outer protective cover toward the body portion is an upward direction and a direction from the body portion of the outer protective cover toward the tip end portion is a downward direction, the inlet-side gas flow channel has a first flow channel that is a space between the outer protective cover and the second member and that extends in the upward direction from the one or more outer inlets and a second flow channel that is a space between the second member and the first member, that is present between the first flow channel and the one or more element chamber inlets, and that extends in the downward direction, a ratio W2/W1 between a flow channel width W1 of the first flow channel and a flow channel width W2 of the second flow channel is less than one, the one or more outer inlets include at least two of three-type holes including a horizontal hole disposed at a side portion of the body portion of the outer protective cover, a vertical hole disposed at a bottom portion of the body portion, and a corner hole disposed at a corner portion at a boundary between the side portion and the bottom portion of the body portion, the tip end portion of the outer protective cover has a tapered portion that reduces in diameter toward a bottom portion of the tip end portion, and the one or more outer outlets include a vertical hole disposed at the bottom portion of the tip end portion of the outer protective cover.

\* \* \* \* \*